United States Patent [19]

Heinrich et al.

[11] Patent Number: 4,638,090

[45] Date of Patent: Jan. 20, 1987

[54] PROCESSES FOR THE PREPARATION OF NITROSAMINE-FREE N,N-DISUBSTITUTED NITROAROMATIC AMINES AND FOR THE STABILIZATION OF THESE COMPOUNDS AGAINST THE FORMATION OF NITROSAMINES

[75] Inventors: Rüdolf Heinrich; Konrad Albrecht, both of Kelkheim, Fed. Rep. of Germany

[73] Assignee: Hoechst Aktiengesellschat, Frankfurt am Main, Fed. Rep. of Germany

[21] Appl. No.: 680,750

[22] Filed: Dec. 12, 1984

[30] Foreign Application Priority Data

Dec. 14, 1983 [DE] Fed. Rep. of Germany ....... 3345157

[51] Int. Cl.$^4$ ............................................. C07C 85/26
[52] U.S. Cl. .................................. 564/437; 564/497; 564/441; 564/411; 564/414
[58] Field of Search ................ 564/437, 497, 441, 411, 564/414

[56] References Cited

U.S. PATENT DOCUMENTS

| | | | |
|---|---|---|---|
| 4,120,905 | 10/1978 | Cannon et al. | 568/933 |
| 4,127,610 | 11/1978 | Eizember | 564/437 |
| 4,136,117 | 1/1979 | Diehl et al. | 564/414 |
| 4,185,035 | 1/1980 | Eizember et al. | 564/437 |
| 4,226,789 | 10/1980 | Eizember et al. | 260/397.7 R |

FOREIGN PATENT DOCUMENTS 0040446  3/1982  Japan ................................. 564/441

OTHER PUBLICATIONS

Nikitenkova, L. P. et al., "Kinetics and Mechanism of the Fischer-Hepp Rearrangement" in J. of Gen. Chem. of USSR, vol. 49, No. 3, Pt. 2, pp. 598–601, Sep. 10, 1979.

*Primary Examiner*—Charles F. Warren
*Assistant Examiner*—John A. Sopp
*Attorney, Agent, or Firm*—Curtis, Morris & Safford

[57] ABSTRACT

Processes for the preparation of nitrosamine-free N,N-disubstituted nitroaromatic amines by degradation of their nitrosamine components formed during their preparation, and by stabilization of the products against renewed formation of nitrosamines, by treating the amines in liquid or molten form with a sulfonic acid, where necessary in the presence of inert organic solvents or diluents.

10 Claims, No Drawings

PROCESSES FOR THE PREPARATION OF NITROSAMINE-FREE N,N-DISUBSTITUTED NITROAROMATIC AMINES AND FOR THE STABILIZATION OF THESE COMPOUNDS AGAINST THE FORMATION OF NITROSAMINES

In the following, N,N-disubstituted nitroaromatic amines are taken to mean N,N-disubstituted aminonitroaromatic compounds which are optionally additionally substituted on the aromatic nucleus, and which were obtained by nitration of the corresponding aromatic starting compounds with concentrated nitric acid, or with nitrating acid (concentrated nitric acid/sulfuric acid) and customary working-up, as well as further reaction of the resulting aromatic nitro compounds, to give the N,N-disubstituted aminonitroaromatic compounds.

N,N-disubstituted aminonitroaromatic compounds are chemically and industrially important compounds in various fields of application such as, for example, in the pharmaceuticals sector and especially in the plant protectants sector.

Of particular economic importance are, for example, the known herbicidal products trifluralin (2,6-dinitro-4-trifluoromethyl-N,N-dipropylaniline), isopropalin (2,6-dinitro-4-isopropyl-N,N-dipropylaniline) and also benfluralin, profluralin, nitralin and oryzalin.

The preparation of, for example, trifluralin is carried out by nitrating 1-trifluoromethyl-4-chlorobenzene with nitric acid in the presence of sulfuric acid to give 1-trifluoromethyl-3,5-dinitro-4-chlorobenzene, from which 2,6-dinitro-4-trifluoromethyl-N,N-dipropylaniline is obtained by amination with the secondary amine, di-n-propylamine. This synthesis can be represented by the following reaction scheme:

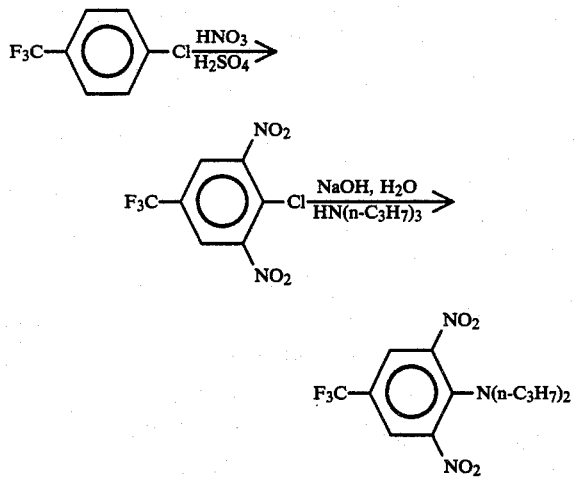

In the preparation, storage and processing of such N,N-disubstituted aminonitroaromatic compounds it is known that, especially at elevated temperatures, the formation of small amounts of dialkylnitrosamines can take place, these compounds being formed from, inter alia, excess secondary amine. Since various nitrosamines of this type exhibited a carcinogenic effect in animal experiments, a man skilled in the art has been increasingly faced with the problem of preparing products which are low in, or free from, nitrosamine, and furthermore of preventing undesired subsequent formation of nitrosamines in the products, the nitrosamine content still tolerated by the authorities, where appropriate, being $\leq 1$ ppm. Modern methods of analysis make it possible to detect the nitrosamines mentioned down to concentrations of 0.1 ppm (0.1 mg/kg).

In trifluralin, for example, nitrosamine is presumably formed by nitrosation of the di-n-propylamine used in the last reaction step by nitrosating agents which are still present in the product, or which are formed thermally from the product, as a result of which the nitrosamine content of the product can rise, for example, to one hundred or more ppm.

The processes developed to date for the removal of nitrosamines are generally based on removing the nitrosation agent which originates from the nitration reaction and which is still present in the reaction product, in order to prevent nitrosation reactions, or decomposing the amounts of nitrosamine already formed, with hydrogen halides, with halogens or with compounds which split off halogen, then treating the product with bases and working up once again.

According to the process in German Offenlegungsschrift No. 2,920,448 (European Patent Application No. 19,281), for removal of the nitrosation components still present from the nitration reaction, the reaction mixture is treated with steam for about 1 hour at 95° to 100° C. and then reacted with the di-n-propylamine.

Similar steps are taken in the process described in German Offenlegungsschrift No. 2,840,551, with the intention of not allowing the formation of any nitrosamines to occur. To this end, the nitrated precursor is freed from any nitrosation agent still present, in the presence of $Na_2CO_3$ or NaOH in the aqueous phase at 50° to 100° C., by passing $N_2$, $CO_2$ or air through the solution for about 1 hour, and subsequently reacted with di-n-propylamine. German Offenlegungsschrift No. 2,926,947 likewise describes a process for purifying the nitrated precursor from nitrosation components by cooling the nitration batch to a temperature below its freezing point, and subsequently separating off the desired pure crystallized precursor.

Although the 3 processes described above serve substantially to remove the components which cause nitrosation of the amine, they lead only to products with a reduced nitrosamine content. Moreover, these methods do not prevent the formation of nitrosamines on prolonged thermal treatment of the dinitroanilines. Thus, investigations have shown that with trifluralin which has been prepared using the purification process described above, the di-n-propylnitrosamine value rose from 0.6 ppm to 2.5 ppm and above after thermal treatment at 70° to 80° C. for 12–15 hours.

German Offenlegungsschrift No. 2,831,119 describes a process for the purification of finished technical trifluralin by treating the latter with aqueous or gaseous hydrochloric acid at elevated temperatures. By this process, which lasts about 2 to 4 hours, the nitrosamine present is destroyed. The hydrochloric acid is subsequently neutralized with $NaHCO_3$, and the purified technical product is worked up again.

In German Offenlegungsschrift No. 2,835,530, the halogens chlorine, bromine and their derivatives bromochloride, N-bromosuccinimide and N-chlorosuccinimide, are used, inter alia, for the decomposition of nitrosamines. A subsequent neutralization with alkali is required also in this case, as well as in the process described in German Offenlegungsschrift No. 2,837,529 for the decomposition of nitrosamines with phosphorus halides, sulfur halides or TiCl₄.

The 3 processes just described result in products which are low in nitrosamine, but require a relatively long thermal treatment of the technical product with subsequent neutralization of the purified product with alkali, and a subsequent working-up step. Moreover, in most cases, they cannot prevent the nitrosamine value from increasing again on prolonged thermal treatment of the product. They do, therefore, result in a reduction of the nitrosamine content to a low level but not in a stabilization against renewed nitrosamine formation.

Thus, all the processes known to date have, inter alia, the disadvantage that they require an additional working-up step and/or do not guarantee sufficient stabilization of industrial N,N-disubstituted aminonitroaromatic compounds on prolonged storage under heat exposure or upon heat treatment.

The object of the invention was therefore to develop a process which overcomes the disadvantages described, and which makes it possible to eliminate nitrosamines, as well as to prevent the formation of fresh nitrosamines in N,N-disubstituted aminonitro-aromatic compounds. Compounds of various chemical structures were therefore investigated for a possible nitrosamine-degrading effect, as well as an effect which would prevent the renewed formation of nitrosamines. Surprisingly, it has been found that sulfonic acids in N,N-disubstituted aminonitroaromatic compounds possess a strong nitrosamine-decomposing effect, and an effect which prevents a possible reincrease in the nitrosamine level. This effect could be attained or detected with, for example, aliphatic, aromatic and araliphatic sulfonic acids, and also with chlorosulfonic and amidosulfonic acids. Both compounds which are soluble in the melt of the N,N-disubstituted aminonitro-aromatic compounds which were to be treated, for example dodecylbenzenesulfonic acid, and also compounds which are insoluble in this melt, such as, for example, p-toluenesulfonic acid, were effective. The required reaction times for complete degradation of the nitrosamines are between about 1 and 10 hours, depending on the reaction temperature, possible reaction temperatures being between 20° and 120° C. Amounts of sulfonic acids of up to about 1% by weight, preferably about 0.05 to 0.5% by weight, based on the N,N-disubstituted aminonitro-aromatic compound used, were required for complete degradation in customary technical products, with subsequent stabilization, depending on the nitrosamine content, solubility in the melt and other reaction conditions.

However, larger quantities than 1% by weight of sulfonic acid can also be added without detriment, if this appears in some cases to be desirable or advantageous for other reasons.

Advantageously, the process is carried out by adding the required amount of sulfonic acid, at a temperature of, for example, between about 50° and 90° C., to the molten N,N-disubstituted aminonitro-aromatic compound containing nitrosamines, and subsequently stirring at this temperature for a few hours. The stirring can be dispensed with for compounds such as dodecylbenzenesulfonic acid, which are soluble in the melt. Working-up procedures are no longer required since the low amounts of sulfonic acid stabilizer required do not in general interfere with the further use of the N,N-disubstituted aminonitro-aromatic product, for example in its formulation as a plant protectant. Sulfonic acid stabilizers which are insoluble in the melt can however also be filtered off, for example in a purification process subsequent to the first formulation step. In particular cases, neutralization with basic compounds shortly before the N,N-disubstituted aminonitroaromatic product is used further, can also be necessary or advantageous.

In contrast to the surprising results of the present invention, it is described, for example in J. Org. Chem. 44, (5) (1979), page 784, that acids such as, for example, p-toluenesulfonic acid, have only very little effect or no effect at all in removing nitrosamines from dinitroanilines, while with sulfuric acid, nitrosamines cannot be degraded but only extracted.

The invention thus relates to a process for the preparation of nitrosamine-free N,N-disubstituted nitroaromatic amines by degradation of their nitrosamine components formed during their preparation, and by stabilization of the products against renewed formation of nitrosamines, wherein the amines are treated in liquid or molten form with a sulfonic acid. According to the invention, by N,N-disubstituted nitroaromatic amines are to be understood the compounds and products discussed and defined at the beginning of the text, pesticidal active substances being preferred.

Examples of substituents on the amine nitrogen atom of the N,N-disubstituted nitroaromatic amines, which can be identical or different, or which can form a heterocyclic ring together with the amine nitrogen atom, are:

Alkyl, alkenyl, alkinyl groups with up to 12 carbon atoms, preferably with up to 5 carbon atoms, which are unsubstituted or substituted, preferably by halogen, in particular Cl or Br, OH, hydroxy-$(C_1-C_4)$-alkyl or cyclo-$(C_3-C_6)$-alkyl, and aryl or araLkyl groups, in particular phenyl or benzyl, which are unsubstituted or are substituted, preferably by halogen, $CF_3$, $(C_1-C_4)$-alkyl, or optionally substituted phenoxy.

The aromatic nuclei of the N,N-disubstituted nitroaromatic amines, which preferably represent benzene rings, in general have, for example, one to three, in particular one or two, preferably two, nitro groups and, if desired, one or more further substituents, in particular, for example, halogen, preferably Cl or Br, $CF_3$, $(C_1-C_{12})$-alkyl, halogeno-$(C_1-C_{12})$-alkyl, $(C_1-C_4)$-alkoxy, halogeno-$(C_1-C_4)$-alkoxy, optionally substituted phenoxy, $(C_2-C_5)$-alkenyl, halogeno-$(C_2-C_5)$-alkenyl, $(C_2-C_5)$-alkinyl, halogeno-$(C_2-C_5)$-alkinyl, $-SO_2-(C_1-C_4)$-alkyl, $-SO_2-NH_2$ and $-CN$.

N,N-disubstituted dinitroanilino compounds are particularly preferred.

Suitable sulfonic acids are:

Aliphatic, aromatic or araliphatic sulfonic acids, preferably with up to 18 carbon atoms, chlorosulfonic acid, amidosulfonic acid, or mixtures of these sulfonic acids.

The amounts of sulfonic acids to be added are not critical. They are based in general on the content of nitrosamine impurities, or of compounds which can potentially form nitrosamines, in the N,N-disubstituted nitroaromatic amine which is to be purified and stabilized.

In customary technical products, the required amounts of sulfonic acids to be added are, in general, up to 1% by weight, preferably 0.05 to 0.5% by weight, based on the N,N-disubstituted nitroaromatic amine to be treated, the latter being mixed with the sulfonic acid in molten or in liquid form, where necessary with addition of inert organic solvents or diluents, and the mixture then being heated for a period of time, preferably 1 to 10 hours, preferably at temperatures of up to 120° C., in particular at from 50° to 90° C., if necessary with stirring.

Stabilization of the technical products mentioned against renewed formation of nitrosamines is particularly required in cases of thermal stress, for example during the melting process, or on prolonged storage, especially at elevated temperatures.

According to the invention, the sulfonic acids to be used, or their reaction products, can remain in the technical product which has been freed from nitrosamines, but they can also be neutralized shortly before the technical product is used further, or they can be filtered off at the first purification step during the further use of the technical product.

Inter alia, the important herbicidal compounds trifluralin and isopropalin are especially suitable as N,N-disubstituted dinitroanilino compounds. Sulfonic acids which can be used according to the invention are, in particular aliphatic sulfonic acids, for example $(C_2-C_{10})$-alkanesulfonic acids, toluenesulfonic acid (o-, m-, p-), 1,3-xylene-4-sulfonic acid, 1,4-xylene-2-sulfonic acid, dodecylbenzenesulfonic acid, isododecylbenzenesulfonic acid, 1-naphthol-4-sulfonic acid, p-aminobenzenesulfonic acid, chlorosulfonic acid and amidosulfonic acid.

The determination of the amounts of nitrosamines was carried out by a gas chromatographic analysis method with a sensitivity down to about $\leq 0.1$ ppm (0.1 mg/kg) (cf. German Offenlegungsschrift No. 2,831,119).

The invention is explained in more detail by the examples which follow.

EXAMPLE 1

50 g of trifluralin with a di-n-propylnitrosamine content of 58 ppm were heated in a stirred flask to 80° C., 0.1 g of p-toluenesulfonic acid was then added, and the mixture was stirred for 5 hours at the above temperature. The product was then allowed to cool without stirring, the p-toluenesulfonic acid settling on the base of the reaction vessel. The di-n-propylnitrosamine content of the trifluralin thus purified was investigated by means of the gas chromatographic method already mentioned. The analysis gave a nitrosamine content of <0.2 ppm.

EXAMPLE 2

50 g of trifluralin with a di-n-propylnitrosamine content of 58 ppm were heated to 80° C., and 0.3 g of dodecylbenzenesulfonic acid were then added. The mixture was stirred for about 5 minutes and then maintained for a further 2 hours at the above temperature. The mixture was then allowed to cool, and a sample was taken for the analytical determination of the nitrosamine content. The analysis gave a di-n-propylnitrosamine content of $\leq 0.1$ ppm.

EXAMPLE 3

50 g of trifluralin with a di-n-propylnitrosamine content of 30 ppm were treated at 80° C. with 0.5 g of butanesulfonic acid, according to the method given in Example 1. A sample was taken after 6 hours for the analytical determination of the nitrosamine content. The analysis gave a di-n-propylnitrosamine content of <0.3 ppm.

EXAMPLE 4

50 g of trifluralin with a di-n-propylnitrosamine content of 30 ppm were treated at 90° C. with 0.3 g of amidosulfonic acid, according to the method given in Example 1. A sample was taken after 8 hours for the analytical determination of the nitrosamine content. The analysis gave a di-n-propylnitrosamine content of <0.3 ppm.

EXAMPLE 5

50 g of trifluralin with a di-n-propylnitrosamine content of 58 ppm were treated at 70° C. with 0.2 g of chlorosulfonic acid, according to the method given in Example 1. After 5 hours a sample was taken, analysis of which gave a di-n-propylnitrosamine content of <0.1 ppm.

EXAMPLE 6

50 g of trifluralin with a di-n-propylnitrosamine content of 30 ppm were treated at 90° C. with 0.3 g of octylbenzenesulfonic acid, according to the method given in Example 1. A sample was taken after 6 hours for the analytical determination. The analysis gave a di-n-propylnitrosamine content of <0.2 ppm.

EXAMPLE 7

50 g of isopropalin with a di-n-propylnitrosamine content of 15 ppm were treated at 70° C. with 0.2 g of p-toluenesulfonic acid as in Example 1. After a reaction time of 3 hours, the di-n-propylnitrosamine content was <0.2 ppm.

EXAMPLE 8

50 g of trifluralin with a di-n-propylnitrosamine content of 30 ppm were treated at 70° C. with 0.2 g of p-toluenesulfonic acid, according to the method given in Example 1. After a reaction time of 5 hours, 50 g of distilled water were added to the product, the mixture was stirred for 30 minutes at 50°[, and brought to pH 8 with sodium carbonate. Stirring was then continued at the above temperature for about a further 30 minutes and the pH was maintained at 8. The nitrosamine content of the aqueous phase and of the treated trifluralin was then investigated. Result: <0.1 ppm di-n-propylnitrosamine in the aqueous phase; <0.2 ppm di-n-propylnitrosamine in the treated trifluraline.

EXAMPLE 9

Nitrosamine degradation and stabilization against a subsequent increase in the nitrosamine content by additives according to the invention 100 g of trifluralin with a di-n-propylnitrosamine content of 0.6 ppm were melted, and the quantity in the batch was halved. 0.3% by weight of dodecylbenzenesulfonic acid was added to one half, and then both samples were stored at 70° C. for 1 week. In the sample to which dodecylbenzenesulfonic acid had been added, the di-n-propylnitrosamine determination gave a di-n-propylnitrosamine content of <0.2 ppm, whereas the di-n-propylnitrosamine content in the non-stabilized sample had risen to 2.5 ppm.

What is claimed is:

1. A process for stabilizing a N,N-disubstituted dinitroaniline compound against the formation of a nitrosamine, which comprises adding an aromatic sulfonic acid with up to 18 carbon atoms to a molten N,N-disubstituted dinitroamiline compound in an amount up to 1% by weight based on the amiline.

2. A process as claimed in claim 1, wherein the aromatic acid is selected from the group consisting of dodecylbenzene sulfonic acid, isododecylbenzene sulfonic acid, a toluene sulfonic acid, 1,3-xylene-4-sulfonic acid and 1,4-xylene-2-sulfonic acid.

3. A process as claimed in claim 1, wherein the aromatic sulfonic acid is added in an amount of 0.05 to 0.5% by weight.

4. A process as claimed in claim 2, wherein the aromatic sulfonic acid is added in an amount of 0.05 to 0.5% by weight.

5. A process as claimed in claim 1, wherein the aromatic sulfonic acid is dodecylbenzene sulfonic acid.

6. A process as claimed in claim 1, wherein the aromatic sulfonic acid is a toluene sulfonic acid.

7. A process as claimed in claim 1, wherein the aromatic sulfonic acid is p-toluene sulfonic acid.

8. A process as claimed in claim 1, wherein the N,N-disubstituted dinitroaniline is selected from the group consisting of trifluralin and isopropalin.

9. A mixture comprising a dinitroaniline compound and an aromatic sulfonic acid in an amount effective for stabilizing the dinitroaniline compound against the formation of a nitrosamine.

10. A mixture as claimed in claim 9, wherein the amount of the aromatic sulfonic acid is up to 1% by weight based on the aniline.

* * * * *